United States Patent
Payton

[11] 4,057,056
[45] Nov. 8, 1977

[54] WALKING CAST

[76] Inventor: Hugh W. Payton, 416 Jupiter St., Washington Court House, Ohio 43160

[21] Appl. No.: 691,447

[22] Filed: June 1, 1976

[51] Int. Cl.² .............................................. A61F 5/04
[52] U.S. Cl. .............................. 128/83.5; 128/89 R
[58] Field of Search ...................... 128/83.5, 83, 87 R, 128/89 R, 90

[56] References Cited
U.S. PATENT DOCUMENTS

| 2,762,367 | 9/1956 | Rubin | 128/83.5 |
| 3,800,789 | 4/1974 | Schloss | 128/90 |
| 3,916,886 | 11/1975 | Rogers | 128/80 E |
| 3,955,565 | 5/1976 | Johnson, Jr. | 128/89 R |

OTHER PUBLICATIONS

Zimmer Fracture Appliances Catalogue, "Lewin Walking Heel", Feb. 1947, p. 116.

Primary Examiner—John D. Yasko
Attorney, Agent, or Firm—Biebel, French & Nauman

[57] ABSTRACT

A premolded walking cast available in a group of sizes, impervious to moisture, and adaptable to variability in swelling for use with fractures or sprains of the lower leg which is lightweight, easy and quick to apply and remove, which eliminates or reduces the need for crutches and which incorporates a removable walker portion.

17 Claims, 20 Drawing Figures

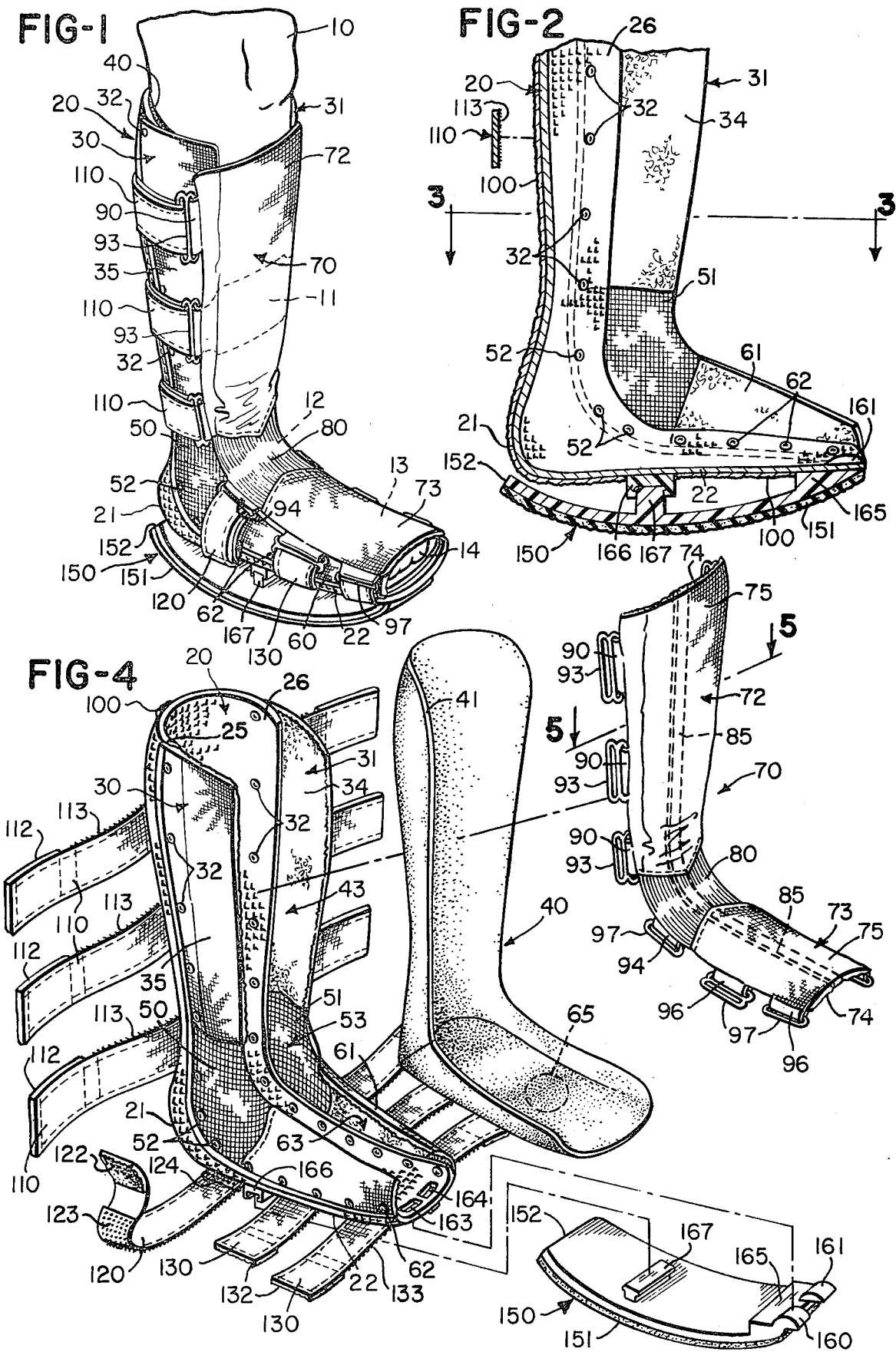

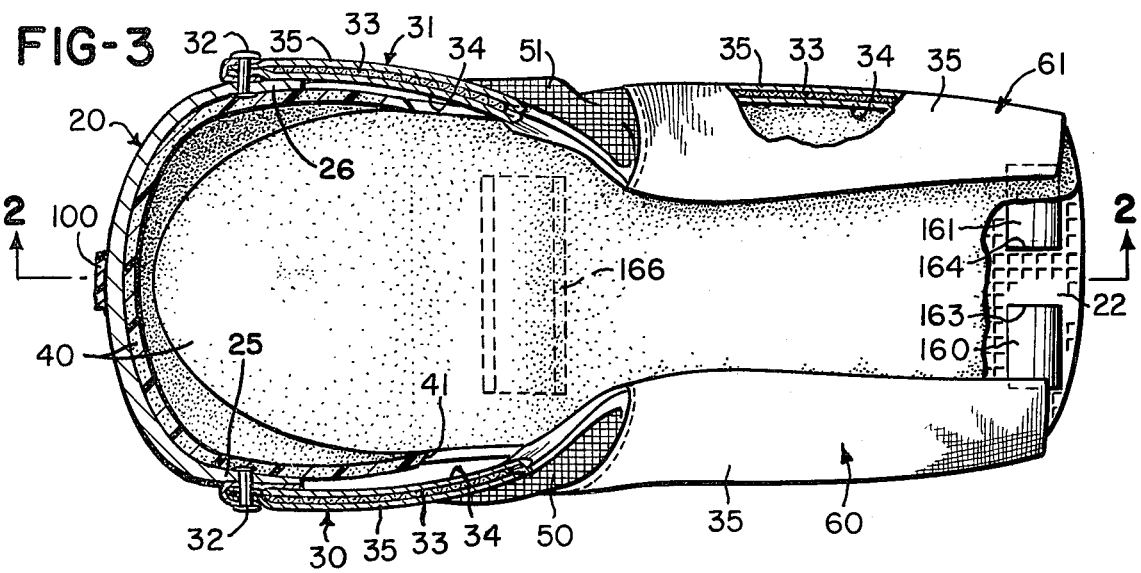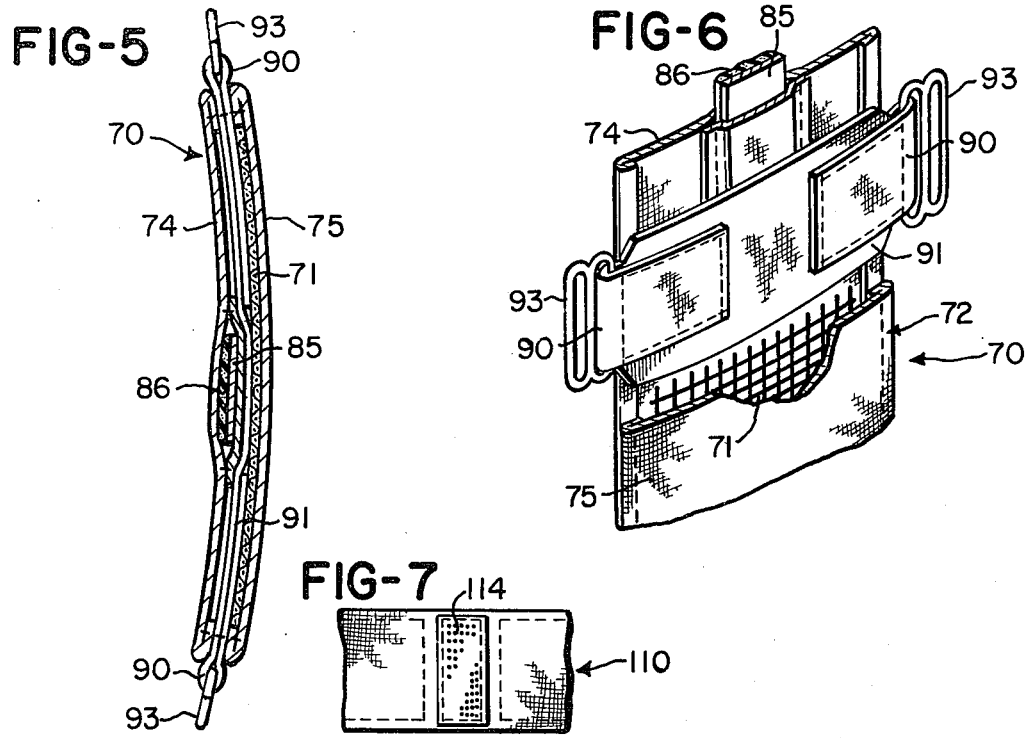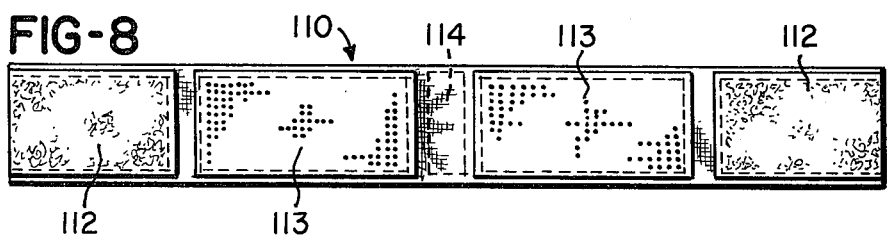

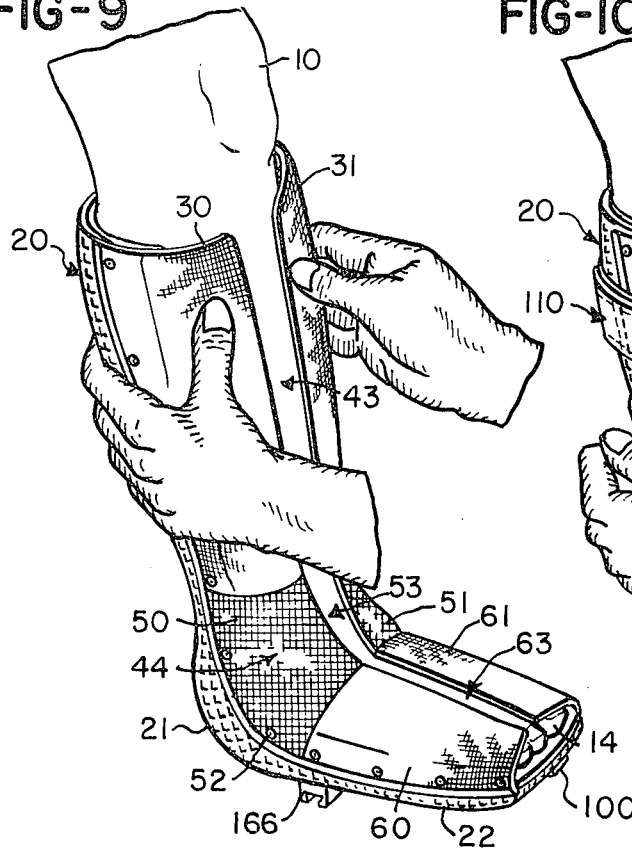
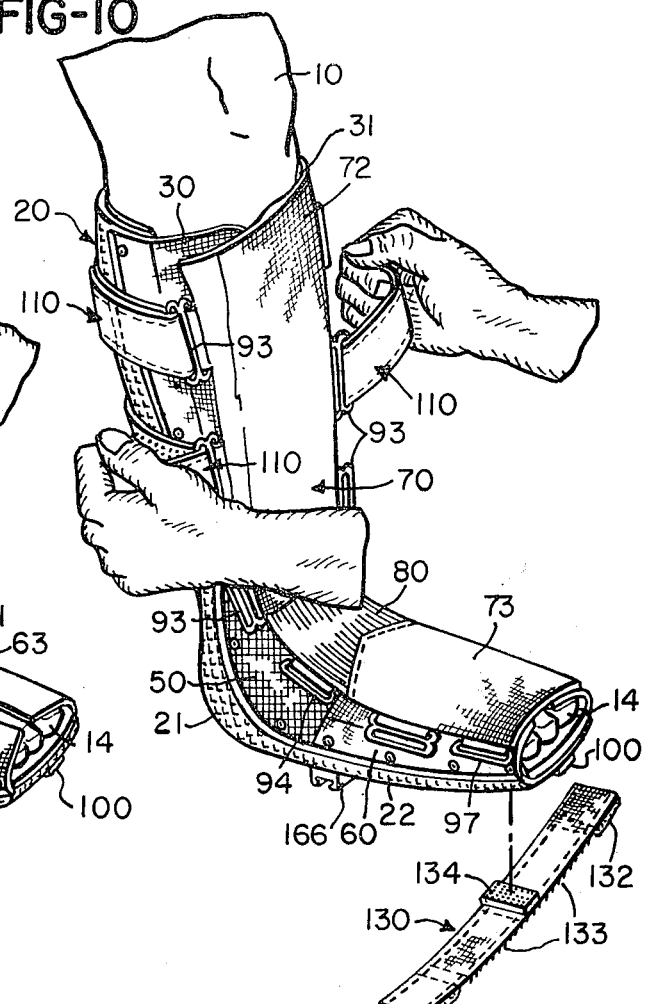
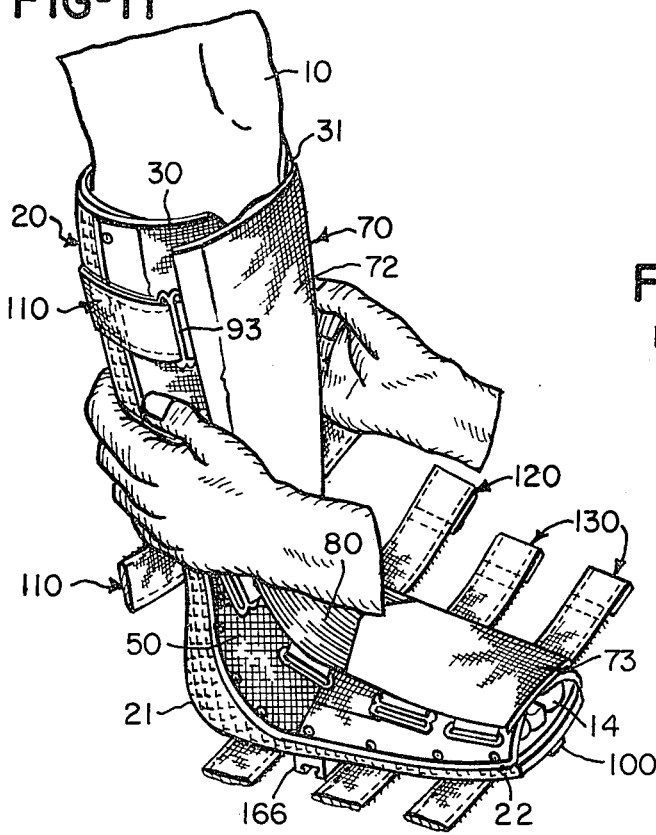
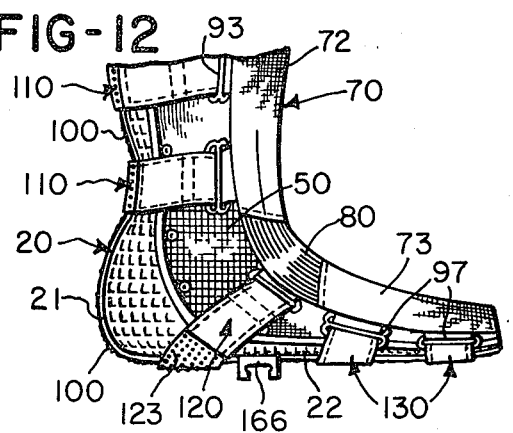

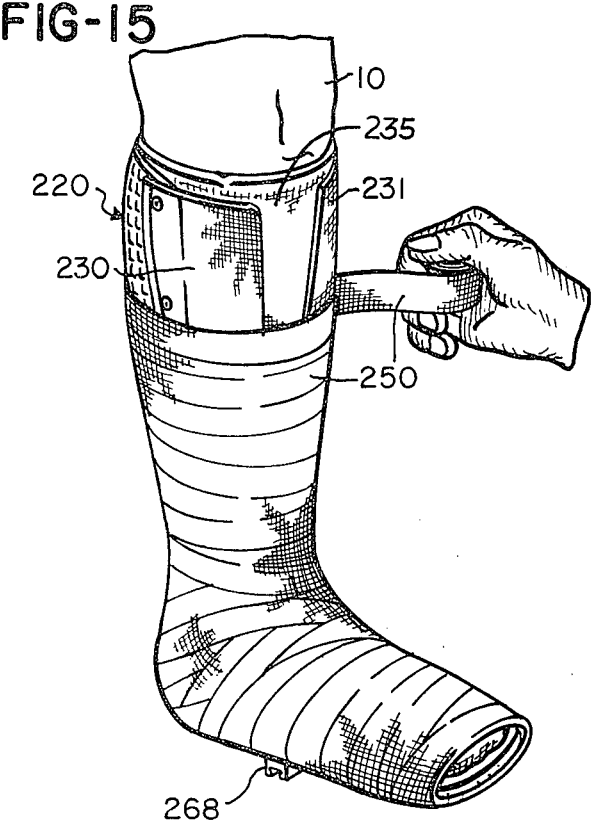
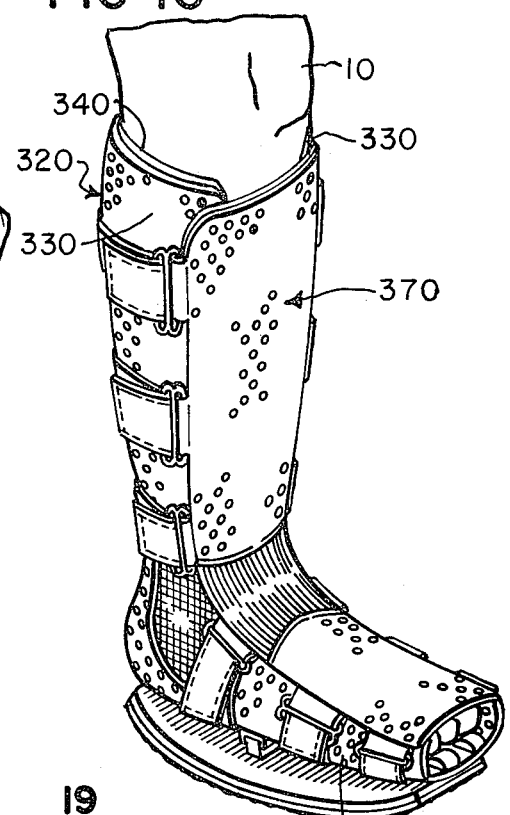
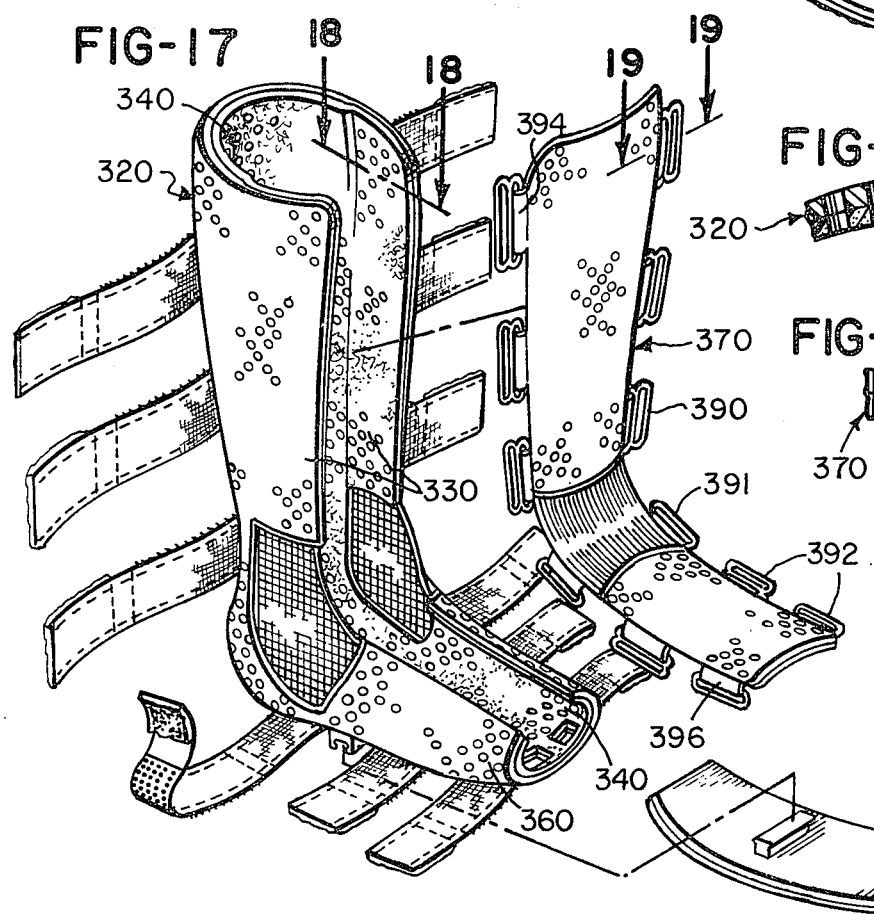
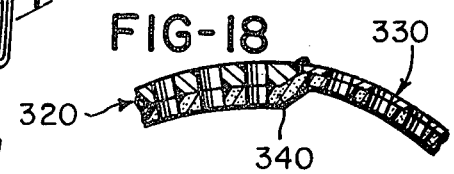
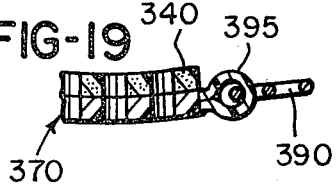

WALKING CAST

BACKGROUND OF THE INVENTION

Fractures of the tibia or fibula, strains or torn ligaments in the ankle or in the foot are usually accompanied by considerable pain and rapid swelling in the area affected. In some cases it is necessary to "set" a fracture, while in other cases, notably a fracture of the fibula, the physician usually does not perform any setting operation. In both situations the important factor is to immobilize the entire lower leg, ankle and foot, after which the healing of the situation occurs by natural processes.

The general problem encountered is well described in prior art patents such as LOAKSO U.S. Pat. No. 3,215,137 of Nov. 2, 1965, QUICK U.S. Pat. No. 3,314,419 of Apr. 18, 1967 and ROSOFF U.S. Pat. No. 3,880,155 of Apr. 29, 1975.

The common practice in the case of what is believed to be a fracture of the lower leg is first to take all weight off the leg, to temporarily immobilize it by the use of splints, bandages or a preformed shell, and to transport the patient to a place of examination and treatment such as a first aid station, an emergency vehicle, or a hospital. The leg is examined usually by a physician, by x-rays, and a determination is made as to whether it needs to be "set", i.e., to have the broken bones aligned. The next procedure is for a physician to apply a plaster of paris cast which is done by wrapping a fabric bandage impregnated with the plaster which has been wet with water, around the entire area in which the fracture occurred. It is likewise common practice to first apply a loose woven sock over which the plaster cast is developed and then allowed to harden. Care must be taken during this operation to insure that the foot is at the normal approximate right-angle position to the leg and that it is also aligned in a proper crosswise direction. As mentioned, it is important that the foot be in a neutral position so that the Achilles tendon is maintained at a proper position. However, when a patient is told to maintain his foot at the neutral right angle position, during the application of the cast, it is common for the patient to allow his foot to droop and in effect the neutral position is not maintained. It is also important that the ventrum of the foot be supported with neither eversion or inversion. However, some inversion tends to be natural and again, the very position of forming a plaster cast often results in inadvertently inducing eversion or inversion. Additionally, in the case of fractures of the small bones of the foot, the surgeon must maintain a proper longitudinal and transverse arch relation, and he does so by physically molding the bottom of the cast into place.

If the plaster cast has not been properly applied or if the cast becomes uncomfortable due to edema or becomes loose due to the fact that it was applied when there was considerable swelling, it may become necessary to saw off the cast and reapply another.

Frequently, the accident which resulted in the need for the walking cast in the first instance has also resulted in a wound which requires stitching and/or dressing. In such instances, it is necessary, after the cast has been applied, to cut a window in the cast for access to the wound area.

Besides all of the other difficulties of plaster casts, they must be maintained totally free of moisture. However, the wearer must get around and many times it is not possible for the wearer to avoid getting the cast wet, particularly along the bottom of the cast which can come into contact with snow or standing pools of water. Further, the bottom of a walking cast is subject to physical abrasion at the toe and heel portions during walking.

While a stockinet or webbing is initially applied, after a period of use it often tends to wrinkle and may actually rot away, leaving the skin of the wearer in direct contact with the plaster resulting in blisters or pressure sores.

Other problems which are not immediately apparent except to physicians include the necessity to estimate the weight and activity of the wearer, in order to determine how thick the plaster should be applied to provide sufficient strength. If the cast is too light for the person involved and his activities, it will crack requiring the same to be removed and replaced.

Plaster casts are made and applied usually in a specific room for this purpose. Not only is this a time consuming process for both parties, it is inherently a messy process. Either the doctor applying the cast must either fully protect his clothing with disposable garments, or he must change his clothes afterwards.

Additionally, many victims of an accident requiring a walking cast are old or infirm or are non-athletic and have great difficulty walking on the cast due not only to their weight but to the position and height of the non-removable walking apparatus applied to the bottom of the cast. The difficulty often poses a real threat of injury to the wearer in getting around. While the cast is drying, a large number of persons will find that they simply cannot or will not manage with the crutches and will lose two or three days of actual time or loss of work and some will utilize crutches or a cane for the entire time cast is worn.

Still further a cast which is worn for an extended period may result in objectionable odor, severe itching and a general sense of discomfort. A prolonged period of immobilization results in loss of muscle power and this can only be restored by use over a period of days or weeks.

Following application of the cast after a short interval, for example, 15 to 30 minutes, the cast has a preliminary set sufficient to allow the patient to walk on crutches, but it is usually 24 to 48 hours before the plaster has set sufficiently to allow weight bearing. The cast applied is relatively heavy, for example of the order of 10 pounds in the case of a large adult male. The cast may be what is known as a "walking cast" in which there may be a circular stem centrally on the bottom side of the cast of a diameter for instance of 2 inches, or it may be a U-shaped walking iron approximately one-half inch in width. In either case there is no broad support and stability is minimal particularly on ice, water and snow. If the stem or walking iron is too far forward or backward so that it alters the center of gravity of walking, this could clearly cause problems.

The intent is for the patient to use the crutches for supporting the major part of his weight while the plaster dries and from that point on to gradually shift the weight from the crutches to the walking cast.

SUMMARY OF THE INVENTION

The cast of the present invention therefore has many important advantages over the plaster now in general use. Since it is premolded and unbreakable it inherently maintains the desired neutral position of the foot and, with the use of proper arch supports, maintains the desired transverse arch. It is disposable and non-allergenic and is easy to apply and to remove.

The appliance is made to be used on either leg, with or without plaster, and with or without a walker. It is adjustable to compensate for swelling and for variable leg contours of the user. Soft tissue injuries or post surgical wounds may be dressed and cared for with ease, without the necessity for a window.

Mobility is greatly enhanced by the ease of use, by a wide and stable non-skid rocking platform which may be removed, by the fact that it is totally impervious to water, is light in weight and eliminates the need for a stockinet or internal webbing. In appropriate instances, the patient may immediately resume activities within a prescribed limit with substantially greater assured safety and comfort. By proper selection of materials, absolute stability is incorporated along a spline portion of the back and the heel while controlled flexibility is incorporated into the sides thereof.

The invention embodies several component parts or segments. One of these parts involves the use of a rigid posterior composite molded shell covering the posterior third of the calf, the ankle and the ventrum of the foot, this part being sometimes hereinafter referred to as the shell. It is preferably foam-lined and perforated in multiple areas both on the calf and the foot area to allow some air circulation while retaining the rigidity necessary to support the weight of the patient and to embrace and immobilize the entire lower leg, ankle and foot of the patient.

Another part of the cast is a pliable foam-lined wrap-around fabric extending from the edges of the shell anteriorly on both sides around the leg, ankle and the foot; these side members approach each other but do not meet in front of the leg, ankle and foot, leaving a gap therebetween. These side members must be pliable enough to conform to the contour of any leg, and further once this conformity has been obtained, the side members preferably should be able to retain this conformity.

At the bend of the ankle, which is a critical area, the shell is relieved and material of the side members is made of a completely stretchable elastic which is very soft and able to conform to the contour of the ankle be it swollen, lacerated, tender or sensitive. Further, the contour of this elastic material is such that it may change from day-to-day as healing and subsidance of swelling in the ankle area occurs.

A further part of the cast involves the use of a tongue likewise formed of pliable foam-lined material similar to that of which the side members are formed, the tongue extending from the top of the cast anteriorly down the front of the leg, ankle and top of the foot. It thus overlies the adjacent edges of the side members and covers the gap therebetween. It carries a series of fasteners preferably in the form of D-rings through which self-gripping fabric fasteners can be inserted which are then secured around the sides and back of the side members and shell to secure all parts in the desired relative positions. Such self-gripping fabric members are capable of easy manual attachment and detachment by the patient or by the physician, and may be retightened, or removed at will.

A further portion of the cast is the walker which comes in contact with the ground. It is made of a rigid plastic material and is detachably secured anteriorly to the toe end of the shell. Suitable means are provided for holding the walker in normal position against the foot of the shell so that it will not fall away when the person picks up his foot in walking. Since the walker member is relatively light in weight, a minimum of force is required to retain it in walking position while permitting release thereof to separate the walker thus enabling the patient to remove the walker when it is time to go to bed.

The walker itself is of wide strap-like contour in width and its longitudinal contour is that of a rocking chair shape extending from the toe back to the heel so that the patient has minimum difficulty in balancing and supporting his weight on the walker without the need for using crutches unless he wishes to do so.

With this arrangement, the party first applying the cast, such as a first-aid volunteer, a paramedic, or a physician, can secure the cast in proper position to support and immobilize the entire lower leg and foot, and the cast may be adjusted after diagnosis from day-to-day as the swelling fluctuates, according to the dictate of the physician.

Even more important, the patient himself can readily release the straps and thereby remove the cast, making it possible for the patient to take a bath and thereafter to reapply the cast himself, always under the limitations prescribed by the particular physician.

In some cases the use of a plaster of paris cast is necessary where for example special molding of the foot, ankle or lower leg is required. In such case, the tongue is omitted and the usual plaster of paris is wound around the shell and side members to cover and enclose the calf, ankle and foot, in the same manner as is now practiced in the conventional cast application. The invention provides the advantage that during this application the foot, ankle and leg are held in the proper neutral positions and when the cast has set, the walker portion may be applied to allow the patient to walk. In this case of course the cast is not removable by the patient, but he still enjoys the advantage of being able to remove the walker portion as desired, and the amount of wrapping may be reduced because the major part of the load on the leg is supported by the shell and not by the plaster itself. Thus the full conventional plaster cast may be, and preferably is, eliminated, or at least its size and weight can be reduced, thereby materially benefiting the patient in returning to walking condition.

BRIEF DESCRIPTION OF THE DRAWINGS

Referring to the drawings which show preferred embodiments of the invention:

FIG. 1 is a perspective view of a walking cast in place on the lower leg, ankle and foot of a patient;

FIG. 2 is a vertical section through the cast on line 2—2 of FIG. 3;

FIG. 3 is a horizontal section on line 3—3 of FIG. 2;

FIG. 4 is an exploded view of the cast of FIG. 1 showing the shell and attached side members, the plastic liner, the tongue, and the detachable walker;

FIG. 5 is a horizontal section through the tongue on the line 5—5 of FIG. 4;

FIG. 6 is a partial perspective view of the tongue with parts being broken away;

FIG. 7 is a fragmentary view of the inner face of one of the fastening straps and showing a male Velcro section;

FIG. 8 is a broken view of the outer face of a strap showing the spaced location of adjacent male and female Velcro sections;

FIG. 9 is a perspective view showing an initial step in applying the cast to a patient's leg and shaping the same to the contours of the calf and foot;

FIG. 10 shows a later step in which the tongue is placed in position on the anterior portion of the calf, ankle and upper portion of the foot with the straps threaded through the D-rings preparatory to being fastened;

FIG. 11 is a similar view showing the way in which the straps are individually tightened to immobilize the leg, ankle and foot in the cast;

FIG. 12 is a side view showing the final position of the cast in place;

FIG. 15 is a perspective view of a modified form of cast in which the conventional plaster of paris wrapping is used;

FIG. 16 is a perspective view of a modified form of cast in which the shell, side members and plastic lining are formed as an integral molded unit;

FIG. 17 is an exploded view of the form shown in FIG. 16; and

FIGS. 18 and 19 are detail sectional views of the lines 18—18 and 19—19, respectively, of FIG. 17.

DESCRIPTION OF THE PREFERRED EMBODIMENT

Figure 13:
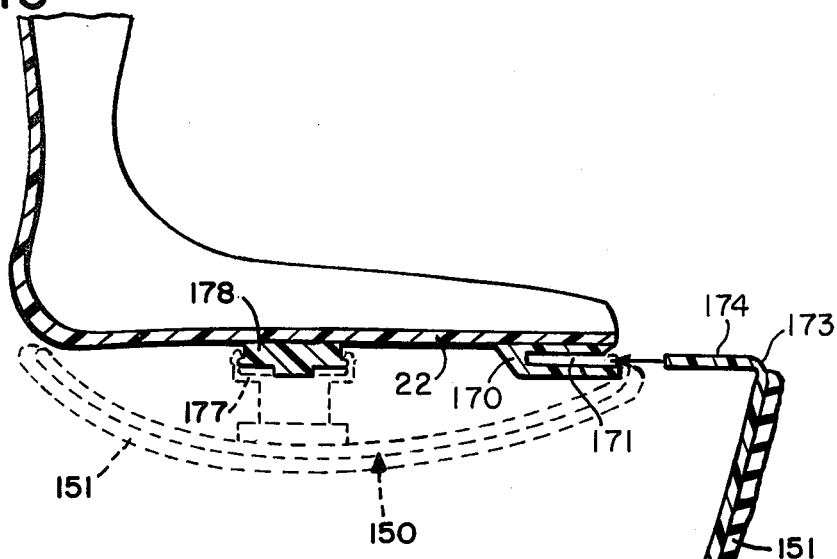
FIG. 13 is a vertical sectional view of a modified form of hinge arrangement for detachably securing the walker section.

Referring to the embodiment shown in FIGS. 1 through 12, the patient's leg is shown at 10 with the anterior portion 11 of the calf, the ankle 12 and the foot 13 and the toes 14 enclosed in the cast of the present invention. The first component of the cast is a rigid non-bendable plastic shell 20 extending from the upper portion of the calf, having a heel portion 21 and a bottom portion 22 on which the foot is supported. A suitable material for this purpose is a polyethylene, polypropylene, etc., plastic. The main shell has side extensions 25, 26 which are pliable to some extent so that when the cast is applied, these side extensions may be molded by manual pressure to conform to the leg size of the individual patient. One of the critical areas is the rear of the heel where protection is afforded for the Achilles tendon and where by the geometry of the shell the maximum bending moments are concentrated, it being important that the shell be completely rigid and non-bending in this area.

Fabric side members 30, 31 are secured to the shell 20 by means of a series of rivets 32, the side members 30, 31 overlying the lateral portions of the leg and being moldable over the anterior portion of the calf and having an interior of woven wire 33 such as that known as hardware cloth. The inner face of the side members is covered by a soft fabric 34 which will not abrade the skin with which it comes in contact, while the outer face of the side members is likewise cloth covered but with a cloth 35 which has water resistant properties and which is capable of being washed. The side members can be manually molded to conform to the shape of the patient's leg and will tend to retain their molded shape.

A liner 40 of plastic foam material is received against the inner face of shell 20 and extends forwardly beyond the shell with skived edges as shown at 41, but terminating short of the side members 30, 31. Thus side members 30, 31 do not overlap but are separated by a gap 43 on the anterior face of the lower leg. The reason for the gap is to allow the cast to conform to and fit the shape of the actual leg to which it is applied, the size and shape of which are subject to considerable normal variation as well as to abnormal variations resulting from the injury. The plastic liner 40 continues over the heel 21 and the foot portion 22 so that the entire lower extremity of the patient rests in contact with the plastic foam material.

In the ankle area the side members 30, 31 are replaced by a stretchable fabric section 50, 51 which overlies the ankle bones or malleoli and which has stretch capabilities in all directions such as the material used in feminine girdles and the like and known as "spandex". It is secured to the shell 20 by suitable means such as rivets 52. This area 50 as shown in FIG. 4, for example, projects from above to a short distance below the ankle, thereby accommodating the malleoli and the entire anterior part of the ankle and allowing for swelling of the area in the ankle zone which usually occurs very shortly after an injury has been sustained. Again, as shown in FIG. 4, the two flexible elements 50, 51 do not overlap but are spaced by a small gap 53 the size of which varies in accordance with the variable contour of the ankle area.

Foot portions of the side members are shown at 60, 61, of substantially the same construction as side members 30, 31 and are likewise spaced from each other thus leaving an open gap 63 which is thus continuous from the top of the gap 20 and including gaps 43 and 53 to the toe area of the cast. These foot elements are secured to the cast 20 by similar rivets 62. Preferably an arch support 65, similar to the conventional transverse arch support used in footwear, is incorporated in the foam rubber lining of the foot portions of the shell.

The cast in its preferred form likewise incorporates a tongue member 70 which is formed with an interior of wire mesh 71 of hardware cloth and the like in its upper and lower portions 72 and 73, similar in all respects to the wire material 33 used in members 30 and 31 and in foot members 60, 61. This wire mesh is enclosed in fabric 74, 75, corresponding to the fabric covers 34, 35 so that the tongue provides a neat and attractive cosmetic appearance when in use on the patient.

In the area immediately overlying the ankle there is a fabric section 80 which is formed of two-way stretch material, i.e., stretchable in the direction of the length of the foot but non-stretchable in the crosswise direction. Material 80 is suitably stitched to the adjacent ends of tongue members 72 and 73, respectively, as shown.

A central strip 85 preferably of aluminum over which there is placed a pad of foam rubber 86 is enclosed in the covering of the tongue and extends throughout its entire length, being located substantially centrally thereof. The strip is for reinforcing and stiffening purposes and is bendable to conform the tongue to the shape of the foot and ankle, including reshaping thereof as the swelling in the ankle and other areas diminishes. Another purpose of the strip 85 is to assure that the tongue will not crease or fold on itself, but will maintain a smooth inner surface and an attractive outer face as well, the rubber pad 86 avoiding any stress application to the skin.

A series of D-shaped fabric loops 90 are secured in spaced relation to the opposite sides of the upper portion 72 of the tongue 70 by suitable taps 91 stitched to the face 75 of the tongue in which there are received metal D-rings 93. Similar D-shaped loops 94 are stitched to the fabric section 80 over the ankle area and another group of D-shaped loops 96 are secured to opposite sides of the lower or foot portion of the tongue 70 with corresponding D-rings 97 in each group.

Attached to the posterior face of the shell 20 is a self-adhering fabric strip 100 which extends down to and around the posterior portion of the heel and on the underside of foot portion 22 of the shell. In place of a continuous strip 100, a series of spaced lengths of this material may be secured in predetermined positions in the proper locations for use with the straps hereinafter described. This material is preferably that known in the trade as "Velcro", and the portion 100 is preferably a female type of such material and will be so described hereinafter although it is to be understood that the terms male and female as applied to such elements and relative only and that either type may be used in conjunction with the other type to achieve the desired fastening effect.

A series of fabric straps 110 are provided in order to secure the various components of the cast with the foot in position. These straps comprise a first group 110 on each side which are adapted to be received through D-rings 93 of the tongue. The terminal portion of each strap 110 has a female fastener section 112 and spaced therefrom are male fastener sections 113 on its outer face as well as a male fastener section 114 on its inner face. Similarly, straps 120 are adapted to be received through D-rings 94 and are provided with female fasteners 122, male fasteners 123 on their outer sides, and a male fastener 124 on the opposite side and centrally of the length thereof but are located clear of the malleoli.

Another series of straps 130 are located in the foot area 22 to be received in D-rings 97 and are provided with female fasteners 132 and male fasteners 133 on their outside and with a male fastener 134 on their inner faces.

To assemble the cast in place, the foam liner 40 is first placed in shell 20 and the leg and foot of the patient located in the position shown in the various figures of the drawing. The sides of the shell 25, 26 are molded to conform to the leg and foot of the patient and the side members 30, 31 and the sides 60 and 61 of the foot are then pressed into position against the foot of the patient. During this operation the ankle areas 50, 51 are not subject to material pressure but are free to conform regardless of the condition of the ankle as to swelling or the like.

The next step involves the placement of the tongue 70 in overlapping relation with the side elements 30, 31, 50, 51 and 60, 61. It likewise is molded manually to conform as closely as possible to the actual shape of the individual patient's calf, ankle and foot.

The next step is to apply the straps by first attaching the straps in proper spaced relation along the fabric fastening strip 100 in the manner and relative position shown in FIG. 4.

In the next operation the straps are extended through the D-rings 93, 94, 97, respectively, and then folded back upon themselves so that their respective female sections 112, 122 and 132 will be received upon and secure themselves to the respective male fasteners 113, 123 and 133. In this position the parts are essentially as shown in FIG. 1 with the entire lower limb of the patient engaged and encased in immobile relation to the cast. After a first application, it is usually found desirable to separate each pair of straps and to tighten the same one by one to thereby secure more firmly the entire leg in proper relation to the cast.

The cast also incorporates a walker portion 150 in the form of a broad rocking chair stiff plastic element such as Lexan, a polycarbonate plastic available from the General Electric Company, and having a lower crepe rubber surface 151. The heel end of the walker shown at 152 is curved upwardly toward the heel of the cast so that if the patient desires to put his foot on a piece of furniture, for example, the rubber covering 151 will protect the latter against damage. The rubber surface affords a safety factor when walking in water, ice or snow.

The walker is made to be removable from the main cast through the use of a hinge comprising spaced tongues 160, 161 which project from the forward edge thereof and are receivable in spaced slots 163, 164 in the toe end of the cast. A bearing plate 165 provides for carrying the weight of the patient at the toe end and an intermediate weight carrying female part 166 on the walker and a male part 167 on the bottom of the cast provide for supporting the weight centrally at the apex of the longitudinal arch of the foot. These weight supporting parts are preferably of yieldable plastic functioning in a manner similar to the conventional cap used on a medicine bottle. These parts 166, 167 are provided with sufficient resiliency so that the male part will normally be retained in the female part during walking action thus forming a releasable retainer means, since it is only necessary that this connection have sufficient strength to carry the limited weight of the walker element. The heel end of the walker is preferably free of contact with the main body of the cast.

The walker is such that it may be readily removed by the patient when it is desired to go to bed. It is only necessary to grasp the heel end of the walker and pull down to swing the hinge members 160, 161 about their axis and the entire walker section may then be separated from the remainder of the cast. The first and foremost reason medically for removing the walker is to enable the patient to remove the walker from the cast at any particular time without in any way reducing or eliminating the immobilization aspects of the cast which are retained throughout. Not only does this reduce the weight for sleeping but also makes it less cumbersome if the patient turns over in his sleep. This removal of the walker portion leaves the bottom of the cast in a clean condition, regardless of what foreign material may have accumulated on the walker during use in the day time. If the physician wants the ankle casted and no weight bearing permitted, he simply does not give the patient the walker.

Figure 13A:
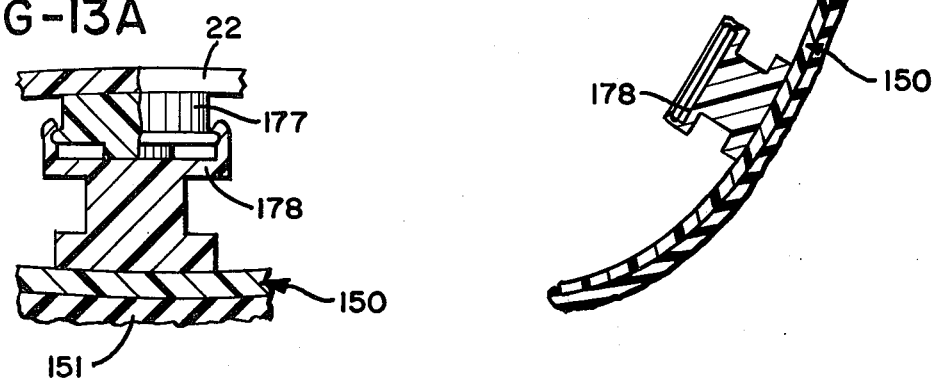
FIG. 13A is a sectional view of a form of releasable retainer for the walker.
Figure 14:
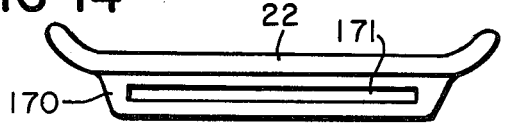
FIG. 14 is an end elevational view of the hinge of FIG. 13.

A modified form of detachable hinge for the walker is shown in FIGS. 13, 13A and 14. In this form the plastic plate 170 on the forward part of the bottom of foot 22 is formed with a forwardly opening slot 171. The walker member 150 has a curved rocking chair bottom portion similar in construction to walker elements 150–152. It is connected by an integral living hinge 173 with a tongue 174 which fits into slot 171 from which it can be easily removed. The same releasable retainer means as described above at 166, 167 may be used, or the retainer may be modified as shown in FIG. 13A to have the male part 177 on the bottom of the shell 22 and the female part 178 on the top of the walker 150.

It thus follows that the invention provides an effective walking cast which affords the same degree of complete immobilization of the lower extremity as if it were protected by the usual plaster of paris cast. At the same time and while the cast is being worn it is much lighter in weight and the walker section gives broad walking support so that the patient in many cases can either dispense entirely with the use of crutches, or can give up the use of crutches much sooner than would otherwise be the case with the normal plaster of paris cast, depending upon the advice of the individual physician.

Another important aspect of the invention is that it is entirely possible and practical for the patient, subject to the instructions of the physician, having once removed the walker, to unfasten the straps, separate the tongue, and step out of the cast without placing weight on the foot, to enable the patient to take a bath whenever such limited degree of movement is permitted by the physician. Following a bath, the patient himself will have no difficulty in replacing his limb in the cast, and refastening the tongue with the same degree of security as when first applied by the physician. At all times, it is within the normal ability of the patient to tighten all retaining straps including those in the overlying area of the ankle, as whatever swelling condition may exist begins to disappear.

Referring now to FIG. 15, the invention also provides for the use of the invention in conjunction with the conventional plaster of paris cast if that should be the procedure desired by the particular physician. In this embodiment the shell 220, the side elements 230 and 231 and all other elements correspond to the similarly numbered elements numbered from 20 through 62 in the first embodiment and function in essentially the same manner. The physician first applies the conventional stockinet, wadding or a long sock 235 to protect the skin from the plaster. There is no tongue however in this embodiment and in place thereof there is shown a plaster of paris tape 250 which is applied in wet form by the physician to entirely encase and immobilize the foot, ankle and calf of the patient in the cast as effectively as in the manner described above through the use of the tongue, the fastening tapes, etc. This embodiment also retains the releasable retainer means 268, 269 for cooperation with a walker similar to that described in the earlier embodiment reference numerals 150 – 167. Thus in this case the patient can be treated through the use of conventional plaster of paris wrapping which however does not need to be as extensive as in the conventional practice because the entire lower limb is held in proper position by being placed in the shell and foot members. Again, the patient has the advantage of a removable walker section to make it easier for night time use but does not have the freedom of removing the cast for bathing, etc., since this type of cast is normally removed only by the physician after x-rays have established the knitting of any fractured bones which may have occurred.

Referring now to FIGS. 16 through 19, a still further embodiment is shown. The significant point of difference in this embodiment is that the shell 320 and the foot portion 360 are made of a perforated premolded plastic having a foam plastic liner 340 formed integrally therewith. A suitable plastic for this purpose is a high molecular weight polyethylene, for example. The remainder of the construction including tongue 370 is essentially similar to that described in the first embodiment except that the side members 330 are formed integrally with the shell 320 and the liner 340 also continues integrally throughout the extent of the side members as shown in FIGS. 17 – 18. Likewise, the D-rings 390, 391, 392 are received through D-loops 394, 396 formed integrally with shell 320 rather than being stitched thereto as in the earlier embodiment.

The invention thus incorporates a highly useful and adaptable orthopedic device which can be used in different ways under the direction of the physician and in conformance with his individual preferences while assuring the fact that the overall weight and cumbersomeness of the cast are greatly reduced, for example, to a third or less. And where the full advantages of the invention are utilized the patient may readjust the cast from time to time as the swelling diminishes and may also remove the cast for purposes of bathing or the like with the assurance that he can replace it in its fully protective position as effectively as if the latter were done by the physician himself.

While the forms of apparatus herein described constitute preferred embodiments of the invention, it is to be understood that the invention is not limited to these precise forms of apparatus, and that changes may be made therein without departing from the scope of the invention which is defined in the appended claims.

What is claimed is:

1. A walking cast for removable attachment to the lower leg of a patient for immobilization thereof comprising,
    a posterior shell of rigid non-bendable material having a contoured shape to receive approximately the posterior third of the calf of the lower leg, the ankle posterior to both malleoli and the ventrum of the entire foot, said shell extending from the upper calf, distally to beneath the lower part of the ankle and the foot, said shell having a shape for rigidly supporting the foot in a predetermined neutral position at substantially right angles to the calf and in proper crosswise relation, the sides of said shell being manually bendable about the calf to conform to the size and body shape of the individual patient,
    pliable side members attached to the sides of said shell and overlying the lateral portions of the leg, ankle and foot with the adjacent edges of said side members being spaced leaving a gap therebetween, said side members being pliable to conform to the contours of the leg, ankle and the foot of the patient,
    and flexible means for closing said gap and confining and securing the calf and foot of the patient in immobilized position embraced within said shell and said side members.

2. A walking cast as defined in claim 1 which the side members overlying the ankle in the zone of the malleoli are of elastic fabric.

3. A walking cast as defined in claim 1 including a fabric tongue covering said gap and overlapping the adjacent edges of said side members.

4. A walking cast as defined in claim 3 including pairs of straps in spaced positions on said tongue and extending over said side members to the posterior portion of said shell to provide for encasing the calf and foot of the patient immobilizing the same in predetermined position in said shell.

5. A walking cast as defined in claim 1 including a walker member removably fastenable to said shell and having a broad support area on which the patient may walk.

6. A walking cast as defined in claim 1 in which there is a stiffening member in the posterior area of said shell extending over the leg embracing portion thereof.

7. A walking cast as defined in claim 1 in which the side member portions adjacent the malleoli are formed of fabric material capable of stretching in all directions.

8. A walking cast as defined in claim 1 in which the inner surface of said shell throughout the extent thereof from the calf portion, the ankle portion and the foot portion is lined with a soft foam rubber-like material.

9. A walking cast as defined in claim 1 in which the shell and the side members are an integral molded unitary element.

10. The cast of claim 1 in which said shell is molded of water impervious non-allergenic synthetic plastic material.

11. The cast of claim 1 in which said shell is formed with a greater thickness at said spine and said bottom than at said sides.

12. A walking cast as defined in claim 5 in which said walker member has a rocking chair shaped ground engaging base, and means for removably attaching said walker member to the bottom of said cast providing for ready separation and removal thereof from said cast.

13. A walking cast as defined in claim 12 in which said walker member is quickly detachable from the cast in response to pivoting motion thereof about an axis adjacent the toe of said molded shell.

14. The cast of claim 12 further comprising means on the outer bottom surface of said shell bottom releasably supporting a ground-engaging walker.

15. A walking cast as defined in claim 4 in which each of said straps is adapted to be held under pressure in locked position by means of fabric self-gripping interlocking fasteners.

16. A walking cast as defined in claim 4 in which the pairs of straps on said tongue are located in the calf area and in the foot area leaving the malleoli free of strap supports.

17. The cast of claim 15 in which said fastening means comprises self-gripping fabric material.

* * * * *